United States Patent [19]

della Valle et al.

[11] Patent Number: 4,737,517

[45] Date of Patent: Apr. 12, 1988

[54] COUMARIN DERIVATIVES, PHARMACEUTICAL COMPOSITIONS CONTAINING THE SAME, AND THE USE THEREOF IN THE TREATMENT OF CANCER

[75] Inventors: Francesco della Valle, Padua; Aurelio Romeo, Rome, both of Italy

[73] Assignee: FIDIA, S.p.A., Abano Terme, Italy

[21] Appl. No.: 635,166

[22] Filed: Jul. 27, 1984

[30] Foreign Application Priority Data

Jul. 29, 1983 [IT] Italy .................. 48791 A/83

[51] Int. Cl.$^4$ .................. A61K 31/37; C07D 311/06
[52] U.S. Cl. .................. 514/457; 549/289
[58] Field of Search .................. 549/289, 403; 514/457

[56] References Cited

U.S. PATENT DOCUMENTS

| 3,515,721 | 6/1970 | Ritter et al. | 549/289 |
| 3,795,685 | 5/1974 | Scanesi | 549/403 |
| 3,880,885 | 4/1975 | Houliban et al. | 549/289 |
| 4,296,039 | 10/1981 | della Valle | 549/289 |
| 4,321,270 | 3/1982 | Sunseen | 514/320 |
| 4,362,741 | 12/1982 | della Valle | 514/457 |
| 4,452,811 | 6/1984 | della Valle | 514/457 |

FOREIGN PATENT DOCUMENTS 2120709  5/1972  Fed. Rep. of Germany ...... 549/403

OTHER PUBLICATIONS

CA 92:146659t p. 582 (1980) Rao et al. Synthesis of Pyranobenzisoxazol-5-ones.
CA 60:15820(g) Mehta et al., Bechnan rearrangement of Oximes of C-acylcoumarins (1964).
Sianesi et al. CA: 77(13):88305(b) 1972, [(Dimethylamino) Cethyl]Coumarins and a Chromenes.
Mathur et al., CA 89:157317u (1978), Antitumor Activity of N-Arylmethyl Nitrogen Mustards.
Shah I et al., 84:30814v (1976), p. 438 Mannich Bases from Halomethyl Coumarins.
Shah II et al. 84:30815w (1976) p. 438 Nitrogen Mustards from Coumarin Derivatives.
Hinshaw et al., CA:98:218134s Fluoresent Chelates & Specific Bending Agents (1983) and vol. 98 Formula Index $C_{26}H_{23}N_3O_{14}$.
"Effect of Warfarin on Survival in Small Cell Carcinoma of the Lung", L. Zacharski et al., JAMA, Feb. 27, 1981, vol. 245, No. 8, pp. 831–835.
"Rationale and Experimental Design for the VA Cooperative Study of Anti-Coagulation (Warfarin) in the Treatment of Cancer", L. Zacharski et al., reprinted from Cancer, vol. 44, No. 2, Aug. 1979, pp. 732–741.

Primary Examiner—Richard L. Raymond
Assistant Examiner—D. L. Dinner
Attorney, Agent, or Firm—Birch, Stewart, Kolasch & Birch

[57] ABSTRACT

A compound having the formula:

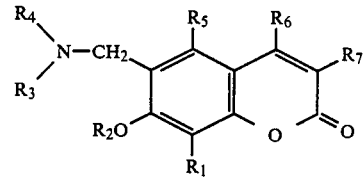

wherein $R_1$ is halogen or a substituted or unsubstituted hydrocarbon group; $R_2$, $R_6$ and $R_7$, which may be the same or different, each represents hydrogen or a substituted or unsubstituted hydrocarbon group, or $R_6$ and $R_7$ taken together may represent a hetero group having one or more hetero atoms; $R_3$ and $R_4$ which may be the same or different each represents a substituted or unsubstituted hydrocarbon group; or $R_3$ and $R_4$ taken together may represent an alkylene group or a hetero group having one or more hetero atoms and $R_5$ is hydrogen, a substituted or unsubstituted hydrocarbon group, halogen or a free or protected hydroxy group, or a pharmaceutically acceptable salt thereof. The compounds have antiaggregating properties.

1 Claim, No Drawings

COUMARIN DERIVATIVES, PHARMACEUTICAL COMPOSITIONS CONTAINING THE SAME, AND THE USE THEREOF IN THE TREATMENT OF CANCER

The present invention relates to new basic coumarin derivatives, procedures for their preparation, pharmaceutical compositions containing them, and methods for their use.

The compounds according to the invention correspond to the following general formula (I):

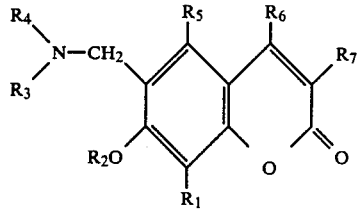

in which $R_2$, $R_5$, $R_6$ and $R_7$ represent hydrocarbyl groups or hydrogen and $R_1$, $R_3$ and $R_4$ represent hydrocarbyl groups and wherein $R_1$ can also represent a halogen and $R_5$ also a halogen or a free or protected hydroxyl group. The hydrocarbyl groups can also be substituted by various functions such as hydroxyl, amino or carbonyl groups, and can be interrupted in the carbon atom chain by heteroatoms such as oxygen, sulfur or nitrogen.

These compounds have antiaggregating properties.

The compounds of the invention are prepared by procedures which are themselves already known, such as by reacting, using a Mannich reaction, the coumarin derivatives corresponding to formula (II):

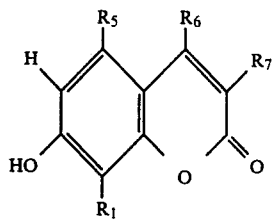

with formic aldehyde and a secondary amine

and if desired, by introducing an $R_2$ hydrocarbyl group into a compound obtained having a free phenolic hydroxyl in the 7-position.

The present invention relates to new basic coumarin derivatives, and in particular the compounds corresponding to the general formula (I):

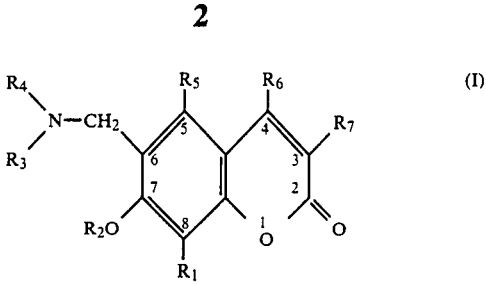

in which $R_2$, $R_5$, $R_6$ and $R_7$ each represent unsubstituted or substituted hydrocarbyl groups which may be interrupted in the carbon atom chain by heteroatoms, or hydrogen; $R_1$, $R_3$ and $R_4$ individually and $R_3$ and $R_4$ jointly, represent unsubstituted or substituted hydrocarbyl groups which may be interrupted in the carbon atom chain by heteroatoms, and $R_1$ may also represent a halogen and $R_5$ may represent a halogen or a free or protected hydroxyl group, their salts, procedures for the preparation of such new compounds and their salts, pharmaceutical compositions containing the same methods for the use of the compounds and their salts.

The compounds of the present invention are active in inhibiting platelet aggregation. They can therefore be used for experimental, diagnostic or therapeutic purposes in veterinary or human medicines and especially as an antithrombotic drug.

One of the objects of the present invention is to provide various preparation procedures for the new coumarin derivatives.

Another object of the present invention is to provide methods for the use of the new coumarin compounds as therapeutic agents.

A further object of the invention is to provide pharmaceutical compositions which contain at least one of the new coumarin compounds as an active ingredient.

These and other objects and advantages of the present invention will become apparent to those skilled in the art from a consideration of the following specification and claims.

The hydrocarbyl groups in formula (I) are aliphatic, araliphatic or alicyclic groups and $R_6$ and $R_7$ may also represent aromatic hydrocarbyl groups. These groups can be unsubstituted or substituted, saturated or unsaturated and can be interrupted in the carbon atom chain by heteroatoms such as oxygen, sulfur or nitrogen. Of the aliphatic groups thus defined, alkyl groups having preferably 1 to 7 carbon atoms and especially from 1 to 4 carbon atoms should be noted. The unsaturated hydrocarbon groups may be alkenyl or polyunsaturated groups such as alkyldienyl, alkyltrienyl and the like having from 1 to 7 carbon atoms, preferably from 1 to 4 carbon atoms. Among the unsaturated aliphatic groups, alkenyl groups having from 2 to 4 carbon atoms are particularly worthy of mention. All of these groups may form linear or branched chains. Of the alicyclic groups as described above, the ones with a simple saturated ring should particularly be mentioned, that is, the cycloalkyl monocyclic groups and especially those with 3 to 7 carbon atoms in the ring, and more particularly from 5 to 7 carbon atoms in the ring. Alicyclic unsaturated groups having 3 to 7, preferably 5 to 7, carbon atoms in the ring may be used. These groups may have one or more double bonds in their cycle, such as the cycloalkenyl groups with a double bond.

Of the unsubstituted alkyl groups, the following preferred groups should be mentioned: methyl, ethyl, propyl, isopropyl, butyl, isobutyl and tert-butyl. Preferred unsubstituted alkenyl groups include vinyl, allyl, propenyl, isobutenyl, 2-butenyl and 2-pentenyl. Exemplary cycloalkyl groups include cyclopropyl, cyclobutyl, cyclopentyl, cyclohexyl and cycloheptyl. Suitable unsubstituted cycloalkenyl groups include cyclopentenyl and cyclohexenyl. The hydrocarbyl aliphatic groups, like the above-mentioned alkyl groups, may however also be substituted by aromatic hydrocarbyl groups, especially for example by phenyl, which may in turn be substituted by various functions, for example from 1 to 3 halogen atoms (particularly chlorine and/or bromine) or by alkyl groups having 1 to 4 carbon atoms such as methyl.

The alicyclic groups include the cycloalkyl and cycloalkenyl groups, such as those mentioned above, having from 3 to 7 and especially between 5 and 7 carbon atoms in the ring, substituted for example by 1 to 3 alkyl groups having for example from 1 to 7, and especially from 1 to 4, carbon atoms, such as methyl, ethyl, propyl and/or isopropyl. The aromatic hydrocarbon groups directly bound to the coumarin ring, such as the $R_6$ and $R_7$ groups, are generally phenyl groups which may be substituted for example by 1 to 3 functions, especially chlorine and/or bromine atoms or by alkyl groups having from 1 to 4 carbon atoms, particularly methyl groups.

The hydrocarbyl groups, and especially the aliphatic and alicyclic groups like all those already mentioned, can be interrupted in the carbon atom chain by heteroatoms, especially by one heteroatom, as in particular by oxygen, sulfur or nitrogen and may be substituted by functions, preferably one or two, for example halogens, free or protected alcoholic functions, free or protected carbonyl groups, free or protected carboxylic groups or free or substituted amine groups.

Halogens are especially represented by fluorine, chlorine and bromine. Among the protected alcoholic functions, etherified or esterified hydroxy groups should have special mention.

The etherifying groups may correspond to each of the above-mentioned hydrocarbyl groups, particularly alkyl groups having 1 to 7, preferably 1 to 4, carbon atoms or cycloalkyl moieties having 3 to 7 carbon atoms in the ring, such as the following groups: methyl, ethyl, isopropyl, cyclopropyl, cyclobutyl and cyclohexyl. The esterified hydroxyl groups may be derived from organic or inorganic acids, for example from acids of the aliphatic, araliphatic, aromatic or alicyclic series, having from 1 to 15 carbon atoms, for example from lower aliphatic acids having from 1 to 7 carbon atoms, such as formic acid, acetic acid, propionic acid, the butyric acids, trimethylacetic acid, caproic acid, succinic acid, phenylacetic acid, benzoic acid, the trimethoxybenzoic acids and the chlorobenzoic acids. The ester groups may also be derived from organic sulfonic acids, especially from alkylsulfonic acids containing from 1 to 7 carbon atoms, such as methanesulfonic acid, or from arylsulfonic acids, such as those containing only one aromatic ring, such as para-toluenesulfonic acid. Ester groups derived from inorganic acids include for example, sulfuric acid, the phosphoric acids and the hydracids, such as hydrochloric or hydrobromic acid.

Among the protected carbonyl functions, the ketal groups should be mentioned, especially cyclic ketal groups, such as those derived from ethylene glycol or propylene glycol. Among the protected carboxylic functions, the esters and amides should especially be mentioned. The esterifying groups may correspond to each of the above-mentioned hydrocarbyl groups, particularly alkyl groups having 1 to 7, preferably 1 to 4, carbon atoms, or cycloalkyl groups having 3 to 7 carbon atoms in the ring, such as methyl, ethyl, isopropyl, cyclopentyl and cyclohexyl.

The amide groups may be the free amido group —$CONH_2$ or an amide substituted at the nitrogen atom, such as the groups derived from the amine groups exemplified below. The amine group can be free or substituted by hydrocarbyl groups, the substituting groups being, for example, the above-mentioned ones, especially alkyl groups having 1 to 7, preferably 1 to 4, carbon atoms, such as methyl, ethyl or isopropyl, or cycloalkyl groups having 3 to 7, preferably from 5 to 7, carbon atoms in the ring thereof, such as cyclopropyl, cyclobutyl, cyclopentyl or cyclohexyl. The amine groups may be derived from primary or secondary amines, that is, one or two of the hydrocarbyl substituent groups may be present. Thus, for example, the amine group may be the —$NH_2$ group or a methylamine, ethylamine, propylamine or dimethylamine group.

These amine groups may in turn be substituted in their hydrocarbyl residues by other functional groups such as a free or protected hydroxyl group, and the free or substituted amine group, such groups being preferably those just mentioned hereinabove. The above-mentioned functions may be found in any position in the chain of carbon atoms of the hydrocarbyl groups, such as in the alpha, beta or gamma position with respect to the coumarin ring. For example, an alkyl group such as $R_1$, $R_6$ or $R_7$ may especially be a —CO—R group, in which R is a hydrocarbyl group, unsubstituted for instance, such as an acyl group, —CO—$CH_3$, —CO—$C_2H_5$, —CO—$C_3H_7$, etc. Specifically, therefore:

$R_1$ may be a hydrocarbyl group as defined, or a halogen, such as fluorine, chlorine or bromine.

$R_2$ may be a hydrogen atom or one of the hydrocarbyl groups previously defined.

$R_3$ and $R_4$ may be, considered separately, one of the hydrocarbyl groups previously defined.

The groups $R_3$ and $R_4$ jointly may also represent a bivalent aliphatic hydrocarbyl group bound to nitrogen by two valences starting from two different carbon atoms (alkylene groups). The alkylene (or alkylenic) groups usually have from 2 to 7 and especially from 2 to 5 carbon atoms and can contain double bonds and be a linear or branched chain. Exemplary alkylene groups include ethylenic, trimethylenic, tetramethylenic, 2-methyltrimethylenic, pentamethylenic, esamethylenic and groups derived therefrom by substitution with one or more methyl or ethyl groups. These hydrocarbyl groups may or may not be substituted by functions, as in the previously mentioned case of the monovalent hydrocarbyl groups and/or they may be interrupted in the carbon atom chain by heteroatoms, such as oxygen, sulfur or nitrogen $$(-NH)$$
$$|$$

in particular. Whenever $R_3$ and $R_4$ jointly represent an alkylene group they form, with the nitrogen atom, heterocyclic monoazotate systems, that is, azacycloalkyl groups, and when the alkylene group represented by $R_3$ and R4 is interrupted by a heteroatom, hetero-azacycloalkyl groups are formed. Of the azacycloalkyl groups, the following are worthy of special mention: pyrrolidino, piperidino, 3-hydroxypiperidino and 4-hydroxypiperidino. Of the bivalent or polyvalent heteroatoms interrupting the carbon atom chain of the alkylenic group R3, R4 the following should especially be mentioned: oxygen, sulfur, nitrogen or the

group which may be substituted by an aliphatic hydrocarbyl group, especially an alkyl group having 1 to 7, particularly 1 to 4, carbon atoms, such as methyl, ethyl or isopropyl, which in turn may be substituted by one or more, for instance from 1 to 3 free or protected hydroxyl groups like those already mentioned, and/or may be interrupted in the carbon atom chain thereof by heteroatoms like those already mentioned above.

Of the hetero azacycloalkyl groups, the following are worthy of special mention: the morpholino, thiomorpholino, piperazino, N-ethylpiperazino and N-hydroxyethylpiperazino rings.

The group $R_5$ is a hydrogen atom or a halogen as previously described for $R_1$ or one of the hydrocarbyl groups also as previously described or a free or protected hydroxyl group. A protected hydroxyl group means an etherified or esterified group as defined above. The etherifying groups are especially $C_1$-$C_7$, preferably $C_1$-$C_4$, alkyl groups such as methyl, ethyl or isopropyl, or cycloalkyl groups having 3 to 7, preferably 5 to 7, carbon atoms in the ring, such as the cyclopentyl and cyclohexyl groups.

The $R_6$ and $R_7$ moieties are both hydrogen atoms or one of the hydrocarbyl groups previously defined by $R_1$ or one of the aromatic hydrocarbyl groups also described above.

Of the compounds of formula (I) according to the invention, preferred are those in which:

$R_1$ is a hydrocarbyl group having from 1 to 7 and preferably from 1 to 4 carbon atoms or a halogen.

$R_2$ is a hydrogen atom or a hydrocarbyl group having from 1 to 7 and preferably from 1 to 4 carbon atoms, possibly substituted by a free carboxylic group or a carboxylic group esterified with an alkyl having from 1 to 7 and preferably 1 to 4 carbon atoms.

$R_3$ and $R_4$ are both alkyl groups with from 1 to 7 and preferably with 1 to 4 carbon atoms and $R_3$ and $R_4$ jointly form an alkylene group with from 2 to 7 carbon atoms which may be interrupted in the carbon atom chain by an atom of oxygen or sulfur or by an —NR— or

group in which R represents an alkyl having 1 to 7 and preferably 1 to 4 carbon atoms which may be substituted by one or more, for instance from 1 to 3 free or etherified hydroxyl groups derived from an aliphatic alcohol having from 1 to 7 and preferably from 1 to 4 carbon atoms or esterified with an organic aliphatic acid having from 1 to 7 carbon atoms.

$R_5$ is hydrogen or a free or esterified hydroxyl group with an aliphatic alcohol having 1 to 7 and preferably 1 to 4 carbon atoms.

$R_6$ and $R_7$ are each and independently hydrogen or an alkyl having 1 to 7 and preferably from 1 to 4 carbon atoms which may be interrupted in the carbon atom chain by a nitrogen atom, or by a —NH— group, or by the —NR— group, in which R represents an alkyl with from 1 to 7 and preferably from 1 to 4 carbon atoms which may be substituted by 1 to 3 free or etherified hydroxyl groups derived from an aliphatic alcohol having from 1 to 7 and preferably from 1 to 4 carbon atoms or esterified with an aliphatic organic acid having from 1 to 7 carbon atoms. The hydroxyl groups may also be substituted with phenyl or phenylalkyl having from 1 to 7 and preferably from 1 to 4 carbon atoms in the aliphatic part and in which groups the phenyl may also be substituted by 1 to 3 methyl groups or by 1 to 3 chlorine or bromine atoms.

Of the products mentioned here, it is worth noting those in which $R_1$ is an unsaturated hydrocarbyl group, especially an alkenyl group having from 2 to 7 carbon atoms, such as the vinyl, allyl, 2-butenyl and isobutenyl groups and wherein $R_3$ and $R_4$ are hydrocarbyl groups, especially alkyl groups having from 1 to 7, preferably 1 to 4, carbon atoms or $R_3$ and $R_4$ jointly with the nitrogen atom constitute a piperazinyl group which may be substituted in the N'-position by an alkyl group with 1 to 4 carbon atoms, which may be terminally substituted by a free hydroxyl, etherified by an alkyl with 1 to 4 carbon atoms or esterified with an aliphatic organic acid having from 1 to 7 carbon atoms. Alternatively, $R_3$ and $R_4$ jointly with the nitrogen atom represent the morpholino or thiomorpholino group or the pyrrolidino or piperidino groups which may be C-substituted by a free or etherified hydroxyl group with an alkyl having 1 to 4 carbon atoms or esterified with an organic aliphatic acid having 1 to 7 carbon atoms.

Of the specific compounds according to the invention, the following are listed as examples:

4-methyl-6-dimethylaminomethyl-7-hydroxy-8-allyl-coumarin 4-methyl-6-(4-morpholinylmethyl)-7-hydroxy-8-allyl-coumarin 4-methyl-6-[[4-(2-hydroxyethyl)-1-piperazinyl]methyl]-7-hydroxy-8-allylcoumarin Ethyl ester of the [4-methyl-6-(4-morpholinylmethyl)-8-allylcoumarin-7-yl]oxyacetic acid 4-methyl-6-(4-morpholinylmethyl)-7-allyloxy-8-allyl-coumarin Ethyl ester of the 2-[4-methyl-6-(4-morpholinylmethyl)-8-allylcoumarin-7-yl]oxy-2-methylpropionic acid 4-phenyl-6-(4-morpholinylmethyl)-7-hydroxy-8-allyl-coumarin 4-phenyl-6-[[4-(2-hydroxyethyl)-1-piperazinyl]methyl]-7-hydroxy-8-allylcoumarin 4-phenyl-6-(4-morpholinylmethyl)-7-allyloxy-8-allyl-coumarin Ethyl ester of the [4-phenyl-6-(4-morpholinylmethyl)-8-allylcoumarin-7-yl]oxyacetic acid Ethyl ester of the 2-[4-phenyl-6-(4-morpholinylmethyl)-8-allylcoumarin-7-yl]oxy-2-methylpropionic acid 4-methyl-6-(1-pyrrolidinylmethyl)-7-hydroxy-8-allyl-coumarin 4-methyl-6-diethylaminomethyl-7-hydroxy-8-allyl-coumarin 4-methyl-6-(1-piperidinylmethyl)-7-hydroxy-8-allyl-coumarin 4-methyl-6-[4-hydroxy-1-piperidinyl)methyl]-7-hydroxy-8-allylcoumarin 4-methyl-6-[(3-hydroxy-1-piperidinyl)methyl]-7-hydroxy-8-allylcoumarin 3-(2-diethylaminoethyl)-4-methyl-6-(4-morpholinylmethyl)-7-hydroxy-8-chlorocoumarin Ethyl ester of the [3-(2-diethylaminoethyl)-4-methyl-6-(4-morpholinylmethyl)-8-chlorocoumarin-7-yl]oxyacetic acid 3-(2-diethylaminoethyl)-4-methyl-6-(4-morpholinylmethyl)-7-allyloxy-8-chlorocoumarin Ethyl ester of the 2-[3-(2-diethylaminoethyl)-4-methyl)-6-(4-morpholinylmethyl)-8-chlorocoumarin-7-yl]oxy-2-methylpropionic acid 4-methyl-6-(4-morpholinylmethyl)-7-hydroxy-8-chlorocoumarin 4-methyl-6-diethylaminomethyl-7-hydroxy-8-chlorocoumarin 4-phenyl-6-(4-morpholinylmethyl)-7-hydroxy-8-chlorocoumarin 3-(2-diethylaminoethyl)-4-methyl-6-(4-morpholinylmethyl)-7-methoxy-8-chlorocoumarin 4-methyl-6-dimethylaminomethyl-7-hydroxy-8-chlorocoumarin 4,8-dimethyl-6-dimethylaminomethyl-7-hydroxycoumarin 4,8-dimethyl-6-(4-morpholinylmethyl)-7-hydroxycoumarin 4-phenyl-6-dimethylaminomethyl-7-hydroxy-8-allylcoumarin The compounds of formula (I) may be salified by known methods and these salts are also an object of the present invention. Of these salts, those obtained by adding acids are particularly important. These are obtained in a conventional manner by treatment with suitable acids. Therapeutically acceptable acids such as hydrochloric, hydrobromic, sulfuric, the phosphoric acids, methanesulfonic, malic, tartaric and succinic acid are suitably used. Nontherapeutic acids may however also be used, thus obtaining salts which can be used for the purification of the products, such as picric acid and picrolonic acid. The compounds of formula (I) in which $R_2$ represents hydrogen may be transformed into metal salts or organic bases by salifying a phenolic group in the 7-position with these bases. These salts are also an object of the invention and may be used in place of the acid-addition salts or free compounds for pharmaceutical or medical purposes. The alkali metal salts, for instance, the sodium and potassium salts, as well as the ammonium salt are worthy of special mention.

The compounds of formula (I) and their salts are active in preventing platelet aggregation. For example, these compounds exhibit this activity in vitro at a concentration of between 10 γ/ml and 1000 γ/ml, as the following experiments show.

Experiment A

Aggregation is evaluated by an aggregometer ELVI 840 according to Born's method (Nature 194, 927, 1962).

New Zealand rabbits are anaesthetized with a mixture of Chloralose and Urethane (40 mg/kg+500 mg/kg), the carotid is cannulated and 40 ml of blood is drawn and 3.8% of sodium citrate is immediately added. Two separate centrifugations are effected (at 1000 rpm and at 6000 rpm), thus obtaining PRP (protein rich plasma) and PPP (protein poor plasma); the first is diluted with the second in order to obtain a platelet concentration of 300,000 per $mm^3$ (the count is effected in a Buerker apparatus). The compounds with a platelet antiaggregating activity of the present invention are added at the desired concentrations and incubated for 30 minutes at 37° C. with the aggregating agents. Platelet aggregation is stimulated by adding ADP at a concentration of 20 μg/ml.

The results are expressed as percentage of inhibition of platelet hyperaggregation induced by ADP added to the PRP in a concentration of 20 μg/ml. The results reported in Table 1 refer to the tests effected with 100 γ/ml of the single compound. The various compounds represented by the numbers in the first column are identifiable by the numbers in the second column which refer to the examples described below in this specification.

TABLE 1

Platelet Antiaggregating Activity

| Compounds | | Inhibition of platelet hyperaggregation induced by ADP (20 μg/ml) at a concentration of 100 γ/ml of the active compound expressed in % |
|---|---|---|
| 19 | (Ex. 1) | 40 |
| 25 | (Ex. 2) | 19 |
| 26 | (Ex. 3) | 23 |
| 27 | (Ex. 4) | 32 |
| 28 | (Ex. 5) | 54 |
| 29 | (Ex. 6) | 19 |
| 44 | (Ex. 7) | 20 |
| 49 | (Ex. 8) | 25 |
| 50 | (Ex. 9) | 25 |
| 51 | (Ex. 10) | 37 |
| 52 | (Ex. 11) | 22 |
| 58 | (Ex. 17) | 25 |
| 62 | (Ex. 18) | 23 |
| 67 | (Ex. 19) | 18 |
| 68 | (Ex. 20) | 41 |
| 69 | (Ex. 21) | 29 |
| 76 | (Ex. 22) | 27 |
| 102 | (Ex. 23) | 12 |
| 105 | (Ex. 24) | 28 |
| 117 | (Ex. 12) | 44 |
| 121 | (Ex. 13) | 51 |
| 124 | (Ex. 14) | 38 |
| 130 | (Ex. 26) | 29 |
| 132 | (Ex. 25) | 13 |
| 188 | (Ex. 27) | 19 |
| 200 | (Ex. 15) | 21 |
| 201 | (Ex. 16) | 32 |

The compounds 4-methyl-6-dimethylaminomethyl-7-hydroxy-8-allylcoumarin and its salts, for example the hydrochloride (compound 19) and 4-methyl-6-[[4-(2-hydroxyethyl)-1-piperazinyl]methyl]-7-hydroxy-8-allylcoumarin and its salts, such as the dihydrochloride (compound 26) also have an antitumoral and antimetastatic activity, as shown by pharmacological experiments carried out in vivo on mice. This activity is to be seen for instance after administration of doses of between 0.2 mg/kg and 10 mg/kg by the oral route, as illustrated by the following experiments.

Experiment B $1 \times 10^5$ 3 LL carcinoma cells (Lewis lung carcinoma) are implanted by intramuscular injection in the paws of male mice of the C57B1/6J strain, weighing about 20-22 g. This operation is effected as described in the literature (Poggi A. et al. Cancer Res. 37, 272-277, 1977). The growth of the tumor is observed until the 25th day after transplant. On this day the animals are sacrificed and the primary tumor and lungs are removed in order to evaluate the growth of the primary tumor and the number of metastases. Pharmacological treatment by the oral route begins 2 days before transplant of the tumor and continues until sacrifice. The substances are dissolved in tap water and are changed every 24 hours.

In a separate experiment, the anticoagulating activity of the compounds is verified on the same strain of mice at the same doses used for antimetastatic activity evaluation.

The effect on coagulation is measured by a thrombotest on capillary blood taken from the retroorbital cavity (Owren, P. A. et al. Lancet ii, 754–758, 1959).

Table 2 reports the results obtained with the two coumarin derivatives 19 and 26, previously mentioned in comparison to Warfarin, the well-known antitumor and antimetastatic compound, which is also a coumarin derivative. Warfarin's antimetastatic activity is widely documented both experimentally (Zacharski, L. R. et al. Cancer 44, 732–741, 1979 and Poggi, A. et al. Lancet i 163–164, 1978) and clinically (Zacharski, L. R. et al. J. Am. Med. Assoc. 245, 831–835, 1981). Indeed, Warfarin has an antimetastatic effect on 'Lewis lung carcinoma', syngeneic with mice of the C57B1/6J strain, causing spontaneous metastasis in the lungs after intramuscular implantation of tumoral cells. This effect is measured by the number of metastases (Zacharski, L. R. et al. Cancer 44, 732–741, 1979 and Poggi, A. et al. Lancet i 163–164, 1978).

Clinically speaking, treatment with Warfarin in association with classic methods such as chemotherapy and radiation, prolongs survival time in patients with lung carcinoma. However, Warfarin in antitumor therapy has the disadvantage of having a strong anticoagulating activity, and it seems that its antitumor action mechanism is mainly linked with this activity. (Donati, M. B. et al. Brit. J. Haematol. 44, 173–182, 1980).

The anticoagulating effect measured by the "thrombotest", the antitumor effect measured by the decrease in weight of the primary tumor and the antimetastatic effect shown as the number of metasteses present in the lungs, are reported in Table 2. While the antitumor and antimetastatic effects of Warfarin and the two new products according to the present invention are roughly equal, the strong anticoagulating effect is absent in the two new products of the invention. This is a completely unexpected result.

aqueous solution. The compounds are administered orally by intubation. Subsequent death may be immediate or may occur at any time up to 14 days after treatment.

The lethal dose 50 ($LD_{50}$), that is, the dose which causes the death of 50% of the animals, is evaluated by the method of Litchfield and Wilcoxon (J. Pharmacol. Ex. Ther. 96, 99–113, 1949). The $LD_{50}$ determined for the two compounds under examination shows low toxicity, as is seen in Table 3.

TABLE 3

| Acute toxicity in the rat of the examined compounds, administered by the oral route in aqueous solution. | | |
|---|---|---|
| Compound 19 | (Ex. 1) | $LD_{50}$ 2 g/kg of body weight |
| Compound 26 | (Ex. 3) | $LD_{50}$ 3.16 g/kg of body weight |

Experiment D

Acute toxicity in the mouse: groups of Swiss mice (male+female) are treated with graduated doses ranging from 0.125 g/kg to 5 g/kg of body weight with compounds 19 to 26. The compounds are administered orally by intubation and dissolved in water.

Subsequent death may be immediate or may occur at any time up to 14 days after treatment. The lethal dose 50 ($LD_{50}$), that is, the dose which causes the death of 50% of the animals, is evaluated by the method of Litchfield and Wilcoxon (J. Pharmacol. Exp. Ther. 96, 99–113, 1949).

Table 4 shows that the compounds are more toxic in the mouse than in the rat. It is, however, a known fact that different results are obtained from a toxicological point of view, according to the animal species considered.

TABLE 4

| Acute toxicity in the mouse of the compounds examined after administration by the oral route in aqueous solution. | | |
|---|---|---|
| Compound 19 | (Ex. 1) | $LD_{50}$ 1.21 g/kg of body weight |
| Compound 26 | (Ex. 3) | $LD_{50}$ 1.95 g/kg of body weight |

The coumarin derivatives of formulas I and IA and their salts, according to the present invention, may be used as platelet antiaggregation drugs for therapeutic and/or prophylactic purposes. The dosages vary according to the conditions, age and state of the patient. Generally, a daily dose by the oral route of about

TABLE 2

| | Antimetastatic activity of coumarin in derivatives compared to Warfarin | | | | |
|---|---|---|---|---|---|
| | Doses | | | | |
| Compounds | 1st Adminis. mg/kg | 2nd Adminis. mg/kg | Thrombotest | Primary Tumor Weight (mg) | No. of metastases |
| Controls | | | 31.4 ± 1.7 | 9087 ± 386 | 21.8 ± 4.9 |
| Warfarin | | | 180 | 6274 ± 690 | 12.4 ± 0.9 |
| 19 (Ex. 1) | 1.5 | 0.3 | 29.3 ± 1.7 | 6731 ± 533 | 11.4 ± 3.3 |
| 26 (Ex. 3) | 2.1 | 0.5 | 33.4 ± 1.2 | 6789 ± 349 | 9.8 ± 2.8 |

The compounds which are the object of the present invention have low toxicity, as can be shown by acute toxicity studies by the oral route in two animal species:

Experiment C

Acute toxicity in the rat: groups of Sprague Dawley rats (male+female) are treated with graduated doses ranging from 0.125 g/kg of body weight to 10 g/kg of body weight of the above mentioned compounds in 20–500 mg for a mammal weighing about 70 kg is advisable.

The procedure for the preparation of the compounds of formula I according to the present invention is as follows:

A. The coumarin derivatives corresponding to formula II:

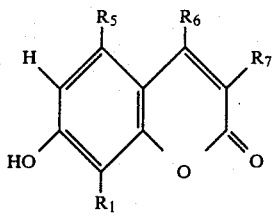

in which $R_1$, $R_5$, $R_6$, and $R_7$ have the same significance as for formula I, are subjected to a Mannich reaction with the secondary amine $NHR_3R_4$ in which $R_3$ and $R_4$ have the same significance as for compound I; or B. Expose to a Claisen or Fries reaction, a compound of formula III:

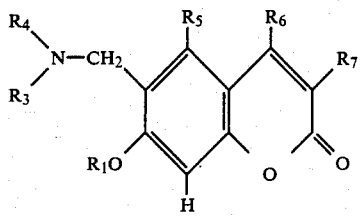

in which $R_3$, $R_4$, $R_5$, $R_6$ and $R_7$ have the same significance as for the compounds of formula I and $R_1$ signifies a possibly substituted hydrocarbyl group, transferable in the 8-position; or C. by means of a Friedel-Crafts reaction, introduce a possibly substituted hydrocarbyl group $R_1$ as defined for formula 1 or introduce a halogen atom $R_1$ by halogenation as defined for formula I in a compound of formula IV:

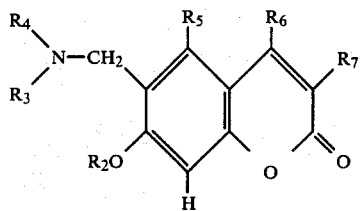

in which $R_2$, $R_3$, $R_4$, $R_5$, $R_6$ and $R_7$ have the same significance as for the compounds of formula I, and $R_2$ may also signify a hydroxyl protection group substitutable by hydrogen and $R_5$ may represent a temporarily protected hydroxyl group; or D. convert the aldehyde group in the 6-position present in a compound of formula V:

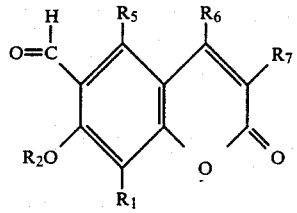

in which $R_1$, $R_2$, $R_5$, $R_6$ and $R_7$ have the same significance as for the compounds of formula I, by reductive alkylation, in the $R_4R_3N$—$CH_2$— group in which $R_3$ and $R_4$ have the same significance as for the compounds of formula I, and $R_2$ may also signify a hydroxyl protection group substitutable by hydrogen and $R_5$ may represent a temporarily protected hydroxyl group; or E. convert a functionally modified hydroxyl group or reagent X present in a compound of formula VI:

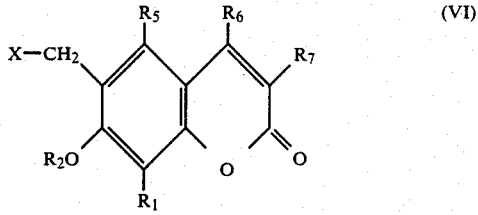

in which $R_1$, $R_2$, $R_5$, and $R_7$ have the same significance as for the compounds of formula I, and $R_2$ may also signify a hydroxyl protection group substitutable by hydrogen and $R_5$ may represent a temporarily protected hydroxyl group, in the $R_4R_3N$— group in which $R_3$ and $R_4$ have the same significance as for the compounds of formula I; or F. convert the —NHZ group into a compound of formula VII:

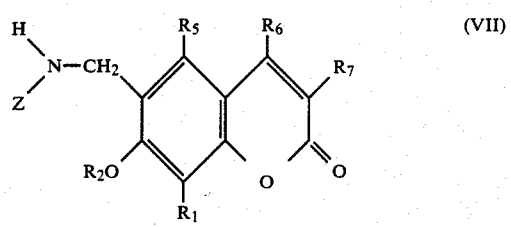

in which $R_1$, $R_2$, $R_5$, $R_6$ and $R_7$ have the same significance as for the compounds of formula I and Z represents hydrogen or one of the $R_3$ or $R_4$ groups having the same significance as for formula I, and $R_2$ may also signify a hydroxyl protection group substitutable by hydrogen and $R_5$ may represent a temporarily protected hydroxyl group, in the —$NR_3R_4$ group; or G. condense by a Pechmann reaction a compound of formula VIII:

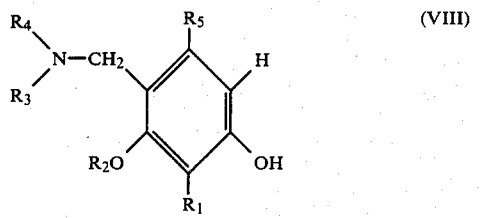

in which $R_1$, $R_2$, $R_3$, $R_4$, and $R_5$ have the same significance as for the compounds of formula I, and $R_2$ may also signify a hydroxyl protection group substitutable by hydrogen and $R_5$ may represent a temporarily protected hydroxyl group, with a compound of formula IX:

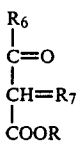

(IX)

in which $R_6$ and $R_7$ have the same significance as for the compounds of formula I and R represents hydrogen or a hydrocarbyl group; or H. condense by a Perkin reaction a compound of formula X:

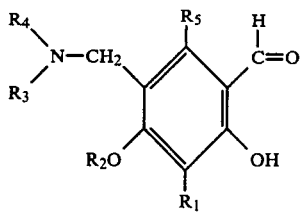

(X)

in which $R_1$, $R_2$, $R_3$, $R_4$, and $R_5$ have the same significance as for the compounds of formula I, and $R_2$ may also signify a hydroxyl protection group substitutable by hydrogen and $R_5$ may represent a temporarily protected hydroxyl group, with a compound of formula XI:

(XI)

in which $R_7$ has the same significance as for the compounds of formula I and R represents hydrogen or a hydrocarbyl group; and if desired, introduce a hydrocarbyl group $R_2$ as defined for formula I into a compound obtained by any one of the previous procedures which has a structure in which $R_2$ represents hydrogen (compound of formula IA) and/or, either before or simultaneously with this introduction, free one or more functional groups from the corresponding functionally modified groups and/or functionally modify the free functional groups and/or interconvert the free functional groups between themselves and/or functionally modify and/or transform an obtained product of formula I or IA into one of its salts.

In the above mentioned procedure A, the Mannich reaction can be conducted in the known manner. The formic aldehyde may be used as such or may be formed in situ, for example using agents which generate formaldehyde, such as the polymeerized or condensed aldehydes, for example paraformaldehyde or hexamethylenetetramine. All of the solvents recommended or described in the literature for the Mannich reaction may be used. The most suitable solvents are aliphatic alcohols, such as those with 1 to 5 carbon atoms, or aliphatic carboxylic acids, such as those with 2 to 4 carbon atoms. In particular, ethyl alcohol or acetic acid, either as such or containing water, is suitably employed.

The amine $HNR_3R_4$ may be used in its free form, or as one of its salts, such as the hydrochloride or sulfate. The secondary amines particularly suitable for the preparation of the compounds (I) are dimethylamine, diethylamine, pyrrolidine, morpholine, piperidine, 3-hydroxypiperidine, 4-hydroxypiperidine, N-ethylpiperazine and N-hydroxyethylpiperazine. Condensation according to Mannich's method is generally effected at a temperature of between about 20° and 120° C., and preferably between about 50° and 90° C..

In procedure B, the above mentioned $R_1$ in the compounds of formula III may be for example an unsaturated aliphatic hydrocarbyl group, particularly an alkenyl group, with a double bond in the beta- or gamma-position, such as an allylic group, which is transferred in the 8-position by applying a Claisen reaction, carried out by a method which is itself well known. For instance, the starting compound is heated to a suitable temperature, such as between 130° and 230° C. with or without a solvent. A tertiary aromatic base, such as dimethylaniline or diethylaniline, can be used as the solvent.

$R_1$ may however also represent a substituted hydrocarbyl group, for instance an acyl group, such as an acetyl, propionyl, butyryl group, etc. In this case, a Fries reaction is used for the transfer of the $R_1$ group in the 8-position and is effected by the known method, for example in the presence of suitable catalysts, such as aluminum chloride in a solvent, which could be for instance carbon disulfide or carbon tetrachloride, at between room temperature and the boiling point of the solvent.

In the above mentioned procedure C, some compounds of formula I are obtained in which $R_1$ may be a substituted or unsubstituted hydrocarbyl aliphatic, araliphatic or alicyclic group, introduced in the 8-position by applying a Friedel-Crafts reaction by the known method.

For example, a suitable derivative containing the $R_1$ group is heated and bound to a halogen or an oxyhydryl (haloid, alcohol) with compound IV at a suitable temperature, such as between 50° and 120° C. in the presence of a solvent and a catalyst. Hydrocarbons such as petroleum ether, carboxylic aliphatic acids such as acetic acid, haloids or organic sulfides such as carbon disulfide may be used as solvents, and Lewis acids, such as boron trifluoride, zinc chloride, aluminum chloride, ferric chloride or sulfuric acid are used as catalysts.

In procedure C, $R_1$ may also represent a chlorine or bromine atom. In this case, a halogenation reaction is used for the introduction of the chlorine or bromine atom, by means of the known method for the halogenation of aromatic compounds. For instance, a compound IV is treated with chlorine or bromine and with one of their derivatives in the presence of a solvent and possibly also a catalyst at a suitable temperature.

In the above mentioned procedure D, the reductive alkylation reaction may be effected in the known way. Aldehyde V is made to react with the amine $R_4R_3NH$ in the presence of a suitable reducing agent. Leukart's reaction is usually used, in which case the reducing agent is formic acid, formamide or methylformate. The reaction is carried out in a suitable solvent, such as the same reducing agent, at a temperature of between 30° and 100° C. In the above mentioned procedure D, the conversion of a functionally modified hydroxyl group X in the group —$NR_3R_4$ is obtained by reaction of the compound of formula VI with the amine $NHR_3R_4$ in a suitable solvent according to a known method. A suitable basic compound may be added to the reaction mixture, for instance an inorganic base such as sodium or potassium carbonate, or tertiary organic bases such as pyridine.

The most suitable solvents for the alkylation reaction are the aliphatic alcohols and aliphatic ketones with between 1 and 5 carbon atoms. A functionally modified and reactive hydroxyl group is especially a hydroxyl group esterified with a hydracid such as hydrochloric, hydrobromic or hydriodic acid, and in this sense X represents chlorine, bromine or iodine, or an organic sulfonic acid such as an alkylsulfonic acid with between 1 and 7 carbon atoms, for example, methylsulfonic acid or ethylsulfonic acid or an arylsulfonic monocyclic acid such as p-toluenesulfonic or benzenesulfonic acid.

In the above mentioned procedure F, one or both of the $R_3$ and $R_4$ groups, as defined for formula I and taken individually and not jointly, are introduced into the —NHZ group of the compound of formula VII where Z represents respectively one of the above mentioned groups or hydrogen, in order to obtain the compound of formula I, for example by an alkylation or reductive alkylation reaction, according to known methods. The alkylation reaction may be carried out using as an alkylating agent a haloid of the $R_3$—Y or $R_4$—Y formula where Y signifies chlorine, bromine or iodine. When starting compounds with the —$CH_2$—$NH_2$ group in position 6 are used, it is possible to introduce two identical $R_3$ or $R_4$ groups using an excess of alkylating agent. With the correct dose of this agent it is possible to introduce just one of the $R_3$ or $R_4$ groups and the compounds thus obtained may be further alkylated, as described above, thus obtaining, if it should be desired, compounds with the two $R_3$ and $R_4$ groups which differ between themselves. The compounds of the two identical $R_3$ and $R_4$ groups may be advantageously obtained by reductive alkylation. Aldehydes with the same number of carbon atoms and the same substitutions present in the $R_3$ or $R_4$ groups may be used as alkylating agents.

In the above mentioned procedure G, the Pechmann reaction may be carried out in the known way. The phenolic compound corresponding to formula VIII is made to react with the carbonyl compound of formula IX in which the R group corresponds to a hydrogen or an alkyl, preferably with between 1 and 4 carbon atoms. The reaction is carried out using the usual condensing agents for the Pechmann reaction, such as sulfuric, hydrochloric and polyphosphoric acid, phosphorus oxychloride, aluminum chloride and zinc chloride.

The reaction is generally carried out at a temperature of between about 0° and 80° C. In some cases it is advisable to use those solvents which are recommended or described in the literature for the Pechmann reaction.

In the above mentioned procedure H, the Perkin's reaction may be carried out in the known way. The aldehyde compound of formula X is made to react with the compound of formula XI in which the R group corresponds to a hydrogen or alkyl, preferably with between 1 and 4 carbon atoms. The reaction is carried out using condensing agents and the solvents recommended or described in the literature for the Perkin's reaction. The reaction is generally carried out at a temperature of between 50° and 110° C..

The optional introduction of a hydrocarbyl $R_2$ group in compounds of formula IA obtained according to any one of the above mentioned procedures may be effected by means of an etherifying reaction using an etherifying agent derived from the $R_2$ hydroxy alcohol. These etherifying agents are for example $R_2X$ alkylation agents, in which $R_2$ signifies a hydrocarbyl group as already described for formula I and X represents a group derived from the functional modification of the hydroxyl, or more precisely, of an ester such as a hydracid ester (and therefore a halogen) or of an inorganic acid such as sulfuric, sulfurous or silicic acid, or of organic sulfonic acids such as the sulfonic acids derived from lower aliphatic hydrocarbons with between 1 and 7 carbon atoms, for example methanesulfonic acid or sulfonic acids derived from aromatic hydrocarbons, especially monocyclic hydrocarbons, such as paratoluenesulfonic or benzenesulfonic acid. X may therefore generally represent a halogen atom, in particular chlorine, bromine or iodine or an alkyl or arylsulfonyloxy, such as the methyl or ethylsulfonyloxy or benzene or p-toluenesulfonyloxy group.

The above mentioned esterification reaction, represented by the following diagram, may be effected in the known manner. The compound $R_2X$ is made to react with the compounds of formula IA or possibly also with their phenolic salts in a suitable solvent.

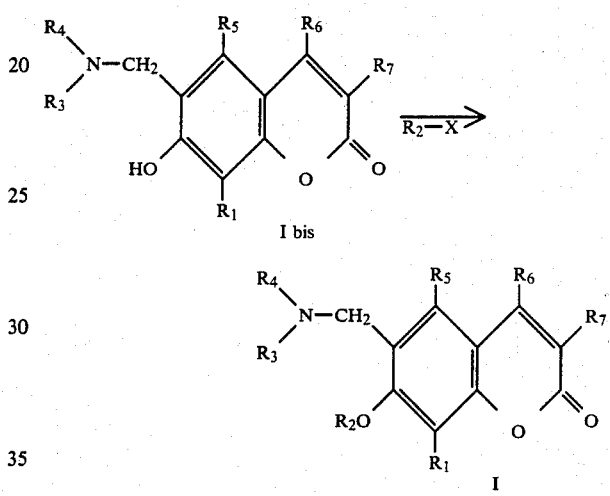

A suitable basic compound should be added to the reaction mixture, for instance, an inorganic base such as hydrates or the basic salts of alkali or alkaline earth metals, such as sodium or potassium carbonate, or tertiary organic bases such as pyridine, quinoline, collidine or Huenig's base.

The most suitable solvents for the previously described alkylation reaction are the aliphatic alcohols such as those with between 1 and 5 carbon atoms, aliphatic ketones or aprotic solvents; in particular acetone, methylethylketone, dimethysulfoxide and sulfolane may be employed.

In some of the preparation procedures for the compounds according to the invention, $R_2$ may represent a protection group of the hydroxyl substitutable by hydrogen, that is, a hydroxyl in the 7-position may be temporarily protected during the reactions of the respective procedures and finally liberated. This temporary protection of the hydroxyl group may take place by functional modification as described in the literature, especially by esterification or etherification. Of the esters, it is worth mentioning those with aliphatic araliphatic or aromatic acids having between 1 and 15 carbon atoms such as those mentioned previously, and also acids which give easily saponifiable esters, for example, halogenated lower aliphatic acids, such as trichloro- or trifluoroacetic acid. These ester groups may then be saponified to give the hydroxyl group by well known methods such as alkaline or possibly acid hydrolysis. Of the ethers, those of tertiary lower aliphatic alcohols such as tert-butyl alcohol, which may be hydrolyzed under acid conditions, can be used. Ethers of aliphatic alcohols such as benzyl or nitrobenzyl alcohol may also be prepared and then separated by reduction in the known way. The same protection groups may also serve to protect, perhaps temporarily, an $R_5$ hydroxyl group which is then liberated in the same way. In an independently known way, moieties present in the hydrocarbyl substituents in the protected form can also be liberated, that is, functionally modified, where the protecting groups are easily eliminated. Vice versa, free functions may, if suitable, be converted into their functional derivatives. The transformation of a functional, free or modified group into another functional group, an object of the general preparation procedure, may be effected according to methods described in the literature.

The compounds obtained according to the above mentioned procedures can be isolated from the reaction mixture in the known way, for example by extraction with organic solvents, such as aliphatic chlorinated hydrocarbides such as methylene chloride, chloroform, dichloroethane, or esters such as ethylacetate, butylacetate, etc.

Before isolating the reaction products, these may be converted into their salts, which may then be purified. From these salts it is possible to obtain the reaction products in the known manner, for instance by adding a base such as a hydrate of an alkali metal or an ammonium compound or with a suitable ion exchanger.

The starting compounds to be used in the above mentioned procedures are well known, as are the methods by which they ar prepared. For example, the compounds II used to prepare derivatives I and IA according to procedure A can be prepared from the resorcinol derivatives of the formula:

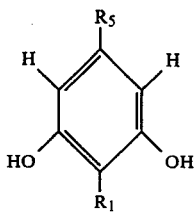

where $R_1$ and $R_5$ have the significance given for formula I by condensation with betacarbonyl acid esters or from coumarin or coumarinic compounds free from any of the desired substituents in which these are introduced. The starting compounds for procedures B, C, D, E, F are generally obtained by methods which are the same as the above mentioned procedures G and H, while the starting products in these procedures may be obtained from resorcinols or fluoroglucines, possibly substituted or functionally modified by known reactions, such as by introduction of the $-CH_2-NR_3R_4$ group by a Mannich reaction similar to that used for procedure A. If the resorcinic or coumarinic starting compounds contain carbonyl reactive functions, such as ketonic functions in particular, it is advisable or necessary to protect them before the various reactions such as the Mannich-type condensation reaction.

Protection of the carbonyl functions for example is effected by one of the known methods such as by action of an ethylene glycol under anhydrous conditions in the presence of acid catalysts. Once the Mannich condensation has been obtained, the carbonyl functions can be regenerated by hydrolysis in an acid aqueous solvent.

The coumarin derivatives of formula I (and therefore also of formula IA) according to the present invention may be used as drugs in pharmaceutical preparations intended for administration to man or animals by intramuscular, subcutaneous or intradermic routes, by injection or intravenous infusion. These preparations may therefore be formulated as solutions of the active compounds or as freeze-dried powders of the active compounds to be mixed with one or more excipients or diluents which are acceptable from a pharmaceutical point of view, and suitable for the above mentioned means of administration and with an osmolarity compatible with physiological liquids.

Furthermore, the therapeutic compounds of formula I (and therefore also formula IA) of the present invention may be in solid or semi-solid form and may be administered by the oral or rectal route, in the form of tablets, sugar-coated pills, gelatinous opercula, suppositories, soft gelatine capsules mixed with pharmaceutically acceptable excipients and suitable for this use, or in the form of creams, ointments or sprays for local, such as topical, use. The preparations according to the present invention generally contain between 0.01% and 10% by weight of the active component for the solutions, sprays, ointments and creams and between 1% and 100%, preferably between 5% and 50% by weight, of the active component for the preparations in solid form. The dosage to be administered depends on the prescription, the desired effect and the chosen route of administration.

The preparations presented in Examples 29 and 30 may be administered directly to animals or human patients by one of the routes described. Examples 29 and 30 show a few possible pharmaceutical compositions which can be prepared for the treatment of platelet hyperaggregation pathology. The pharmaceutical compositions shown in Example 29 are prepared using a double container made of glass. The first contains the active substance in the form of a freeze-dried powder together with a pharmaceutically acceptable excipient. The second container is filled with the desired quantity of solvent. Not until just before administration are the contents of the two flacons mixed and the active substance, in the form of a freeze-dried powder, is rapidly dissolved to produce an injectable solution. The pharmaceutical form preferred by the present invention is that which consists of a container holding the active substance as a freeze-dried powder, as the active substance has proved to be more stable in a dry, powdered form than in solution.

Example 30 shows pharmaceutical preparations to be used by the oral route in pathologies connected with platelet hyperaggregation. The preparations may also be formulated in a gastroresistant form.

The present invention also includes modifications of the above mentioned procedures, where the procedures are interrupted at a certain point, or where an intermediate compound is used to begin with, after which the subsequent stages are carried out, or where the starting products are formed in situ. The following examples amply illustrate the products, the preparation procedures and the pharmaceutical preparations of the present invention, but are not to be considered as limiting. Unless otherwise noted, the percentages therein and throughout the application are by weight and the temperatures are in degrees Centigrade.

EXAMPLE 1

4-methyl-6-dimethylaminomethyl-7-hydroxy-8-allyl-cumarin hydrochloride.

30 g of 4-methyl-7-hydroxy-8-allylcourmarin are mixed with 350 ml of ethanol, 24.3 g of dimethylamine aqueous solution at 33% and 5.5 g of paraformaldehyde. The mixture is refluxed for 48 hours, while being continuously agitated; the ethanol is then evaporated in vacuum. The residue is gathered with ethyl acetate and the organic solution is extracted with 1N hydrochloric acid. The acid aqueous layer is alkalinized with sodium bicarbonate and extracted with ethyl acetate. The ethyl acetate extract is dried on anhydrous sodium sulfate and, after filtration, is concentrated to a small volume; precipitation of the crystalline hydrochloride is achieved by adding gaseous hydrochloric acid. The precipitate is separated and crystallized from ethanol; when the crystals have been filtered and dried, the hydrochloride of 4-methyl-6 -dimethylaminomethyl-7-hydroxy-8-allylcourmarin is obtained.

MP 216°, Rf 0.46 [thin layer chromatography (silica) chloroform-methanol-acetic acid-water (25+15+4+2)].

EXAMPLE 2

4-methyl-6-(4-morpholinylmethyl)-7-hydroxy-8-allyl-cumarin hydrochlorode 32.4 g of 4-methyl-7-hydroxy-8-allylcoumarin are mixed with 300 ml of ethanol, 13 g of morpholine and 4.5 g of paraformaldehyde. The mixture is heated to 60° for 48 hours, being continuously agitated in the meantime; the ethanol is then evaporated in vacuum. A saturated solution of sodium bicarbonate is added to the residue and the mixture is then extracted with methylene chloride. The organic solution is extracted 3 times with hydrochloric acid 1N and the aqueous acid layer is neutralised with aqueous ammonium hydroxide at 32%; a suspension is thus formed which is then filtered. The precipitate is vacuum dried and then treated with ethyl acetate; precipitation of the crystalline hydrochloride is achieved by addition of gaseous hydrochloric acid. The precipitate is separated and then crystallised by ethanol; after filtration and drying of the crystals, hydrochloride of 4-methyl-6-(4-morpholinylmethyl)-7-hydroxy-8-allylcoumarin is obtained.

MP 234°, Rf 0.78 [thin layer chromatography (silica) chloroform-methanol-water-ammonium hydroxide 32% (130+25+2.8+0.5)].

EXAMPLE 3

4-methyl-6-[[4-(2-hydroxyethyl)-1-piperazinyl]methyl]-7-hydroxy-8-allylcumarin dichlorohydrate 21.6 g of 4-methyl-7-hydroxy-8-allylcourmarin are mixed with 250 ml of ethanol, 16.9 g of 1-(2 hydroxyethyl)piperazine and 11.2 g of formaldehyde aqueous solution at 35%. The mixture is heated to 70° for 48 hours, being continuously agitated meanwhile; the ethanol is then evaporated in vacuum. A saturated solution of sodium bicarbonate is added to the residue and the mixture is extracted with methylene chloride. The organic solution is extracted 3 times with hydrochloric acid 1N and the acid aqueous layer is alkalized with bicarbonate of soda and extracted with toluene. The toluenic solution is dried on anhydrous sodium sulfate, filtered and the solvent is then eliminated in vacuum. The residue is gathered with ethyl acetate and the formation of crystalline hydrochloride is achieved by adding gaseous hydrochloric acid. The precipitate is separated and crystallised with 95% ethanol; after filtration and drying of the crystals dichlorohydrate of 4-methyl-6-[[4-(2-hydroxyethyl)-1-piperazinyl]methyl]-7-hydroxy-8-allylcourmarin is obtained.

MP 201°, Rf 0.52 [thin layer chromatography (silica) chloroform-methanol-water-ammonium hydroxide 32% (130+25+2.8+0.5)].

EXAMPLE 4

Ethyl ester of the acid [4-methyl-6-(4-morpholinylmethyl)-8-allylcumarin-7-yl]oxyacetic 16 g of 4-methyl-6-(4-morpholinylmethyl)-7-hydroxy-8-allylcoumarin are mixed with 300 ml of toluene and 1.25 g of sodium hydride. The mixture is gradually heated to 60°, being continuously agitated meanwhile; after thirty minutes' heating the solvent is evaporated in vacuum. The residue is solubilised with 100 ml of dimethylsulfoxide and to this solution, kept at room temperature, 9.8 g of ethyl chloroacetate are added; after twelve hours 300 ml of toluene are added and the organic mixture is washed with water. The toluenic solution is reduced to a small volume in vacuum and the formation of crystalline hydrochloride is achieved by adding gaseous hydrochloric acid. The precipitate is separated and then crystallized in ethanol; after filtering and drying the crystals, hydrochloride of 4-methyl-6-(4-morpholinylmethyl)-7-(ethoxylcarbonylmethoxy)-8-allylcoumarin is obtained.

MP 176°, Rf 0.85 [thin layer chromatography (silica) chloroform-methanol-acetic acid-water (25+15+4+2)].

EXAMPLE 5

4-methyl-6-(4-morpholinylmethyl)-7-allyloxy-8-allyl-cumarin hydrochloride 16 g of 4-methyl-6-(4-morpholinylmethyl)-7-hydroxy-8-allylcoumarin are treated as in the case of example 4 until precipitation of the hydrochloride. 6.1 g of allyl bromide are used in place of the ethyl chloroacetate. The precipitate is separated and crystallised in ethanol; after filtering and drying the crystals hydrochloride of the 4-methyl-6-(4-morpholinylmethyl)-7-allyloxy-8-allyl coumarin is obtained.

MP 203°, Rf 0.76 [thin layer chromatography (silica) chloroform-methanol-water-ammonium hydroxide 32% (130+25+2.8+0.5)].

EXAMPLE 6

Ethyl ester of the acid 2-[4-methyl-6-(4-morpholinylmethyl)-8-allylcumarin-7-yl]oxy-2-methylpropionic hydrochloride 9.5 g of 4-methyl-6-(4-morpholinylmethyl)-7-hydroxy-8-allylcoumarin are mixed with 300 ml of toluene and 0.8 g of sodium hydride. The mixture is gradually heated to 60°, being constantly agitated meanwhile; after 30 minutes' heating the solvent is evaporated in vacuum. The residue is solubilised with 100 ml of dimethylsulfoxide and 5.9 g of ethyl α-bromoisobutyrate are added to the solution which is kept at a temperature of 60°. After 48 hours 300 ml of toluene are added and the organic mixture is washed with water. The toluenic solution is reduced to a small volume in vacuum and formation of crystalline hydrochloride is achieved by addition of gaseous hydrochloric acid. The precipitate is separated and crystallised with ethanol; after filtering and drying the crystals, hydrochloride of the ethyl ester of the 2-[4-methyl-6-(4-morpholinylmethyl)-8-allyl-coumarin-7-yl]oxy-2-methylpropionic acid is obtained.

MP 171°, Rf 0.79 [thin layer chromatography (silica) chloroform-methanol-water-ammonium hydroxide 32% (130+25+2.8+0.5)].

EXAMPLE 7

4-phenyl-6-(4-morpholinylmethyl)-7-hydroxy-8-allyl-cumarin hydrochloride 20 g of 4-phenyl-7-hydroxy-8-allylcoumarin are mixed with 200 ml of 80% aqueous ethanol, 6.3 g of morpholine and 6.2 of 35% formaldehyde aqueous solution. The same procedure as in the case of example 1 is used until precipitation of the hydrochloride. The precipitate is separated and crystallised with ethanol; after filtering and drying the crystals, hydrochloride of 4-phenyl-6-(4-morpholinylmethyl)-7-hydroxy-8-allyl-coumarin is obtained.

MP 208°, Rf 0.87 [thin layer chromatography (silica) chloroform-methanol-water-ammonium hydroxide 32% (130+25+2.8+0.5)].

EXAMPLE 8

4-phenyl-6-[[4-(2-hydroxyethyl)-1-piperazinyl]methyl]-7-hydroxy-8-allylcumarin dihydrochloride 15 g of 4 phenyl-7-hydroxy-8-allylcoumarin are mixed with 200 ml of ethanol, 7 g of 1-(2-hydroxyethyl)-piperazine and 4.6 g of 35% formaldehyde aqueous solution. The mixture is refluxed for 48 hours, being kept in constant agitation meanwhile. The ethanol is then evaporated in vacuum. The residue is gathered with ethyl acetate and the organic solution is extracted with hydrochloric acid 1N. The aqueous acid layer is alkalinized with sodium bicarbonate; a suspension is formed which is then filtered. The precipitate is vacuum dried and then treated with ethyl acetate; precipitation of the crystalline hydrochloride is achieved by adding gaseous hydrochloric acid. The precipitate is separated and crystallised with ethanol; after filtering and drying the crystals, dihydrochloride of 4-phenyl-6-[[4-(2-hydroxyethyl)-1-piperazinyl]methyl]-7-hydroxy-8-allylcourmarin is obtained.

MP 250°, Rf 0.74 [thin layer chromatography (silica) chloroform-methanol-acetic acid-water (25+15+4+2)].

EXAMPLE 9

4-phenyl-6-(4-morpholinylmethyl)-7-allyloxy-8-allyl-cumarin hydrochloride 20 g of 4-phenyl-6-(4-morpholinylmeythyl)-7-hydroxy-8-allylcoumarin are mixed with 300 ml of toluene and 1.35 g of sodium hydride. The mixture is gradually heated to 60°, being constantly agitated in the meantime. After 30 minutes' heating the solvent is evaporated in vacuum. The residue is solubilised with 100 ml of dimethylsulfoxide and 6.4 g of allyl bromide; after 12 hours 300 ml of toluene are added and the organic mixture is washed with water. The toluenic solution is extracted with hydrochloric acid 1N and the aqueous solution is alkalinized with sodium carbonate and then extracted with methylene chloride. The methylene chloride solution is dried on anhydrous sodium sulfate and the solvent is eliminated in vacuum after filtration. The residue is gathered with toluene and formation of crystalline hydrochloride is achieved by adding gaseous hydrochloric acid. The precipitate is gathered and then crystallised with ethanol; after filtering and drying the crystals, hydrochloride of 4-phenyl-6-(4-morpholinylmethyl)-7-allyloxy-8-allylcoumarin is obtained.

MP 208°, Rf 0,87 [thin layer chromatography (silica) chloroform-methanol-water-ammonium hydroxide 32% (130+25+2.8+0.5)].

EXAMPLE 10

Ethyl ester of [4-phenyl-6-(4-morpholinylmethyl)-8-allylcumarin-7-yl]oxy acetic acid hydrochloride 24 g of 4 phenyl-6-(4-morpholinylmethyl)-7-hydroxy-8-allylcoumarin are mixed with 300 ml of toluene and 1.6 g of sodium hydride. The mixture is gradually heated to 60°, being constantly agitated meanwhile; after 30 minutes' heating the solvent is evaporated in vacuum. The residue is solubilised with 100 ml of dimethylsulfoxide and 8 g of ethyl chloroacetate are added to the solution, which is kept at a temperature of 60°; after 24 hours 300 ml of toluene are added and the organic mixture is washed with water. The toluenic solution is extracted with hydrochloric acid 1N and the acid aqueous solution is alkalinised with sodium bicarbonate. A suspension is thus formed which is then filtered. The precipitate is vacuum dried and then gathered with toluene; the precipitation of the crystalline hydrochloride is achieved by adding gaseous hydrochloric acid. The precipitate is separated and then crystallised with ethanol; after filtering and drying the crystals, the hydrochloride of the ethyl ester of [4-phenyl-6-(4-morpholinylmethyl)-8-allylcoumarin-7-yl]oxy acetic acid is obtained.

MP 108°, Rf 0.88 [thin layer chromatography (silica) chloroform-methanol-water-ammonium hydroxide 32% (130+25+2.8+0.5)].

EXAMPLE 11

Ethyl ester of 2-[4-phenyl-6-(4-morpholinylmethyl)-8-allylcumarin-7-yl]oxy-2-methylpropionic acid hydrochloride 20 g of 4-phenyl-6-(4-morpholinylmethyl)-7-hydroxy-8-allylcoumarin are mixed with 300 ml of toluene and 1.35 g of sodium hydride, the mixture is gradually heated to 60°, being constantly agitated meanwhile. After thirty minutes' heating the solvent is evaporated in vacuum. The residue is solubilized with 100 ml of dimethylsulfoxide and 11.7 g of ethyl α-bromoisobutyrate are added to the solution, which is kept at a temperature of 60°.

After 72 hours 300 ml of toluene are added to the organic mixture which is then washed with water. The toluenic solution is extracted with hydrochloric acid 1N and the aqueous solution is alkalinized with sodium bicarbonate; a suspension is thus formed which is subsequently filtered. The precipitate is vacuum dried and then gathered with toluene; precipitation of the crystalline hydrochloride is achieved by adding gaseous hydrochloric acid. The precipitate is separated and crystallized with ethanolic solution by adding ethyl acetate; after filtering and drying the crystals, hydrochloride of the ethyl ester of 2-[4-phenyl-6-(4-morpholinylmethyl)-8-allylcoumarin-7-yl]oxy-2-methylpropionic acid is obtained.

EXAMPLE 12

4-methyl-6-(1-pyrrolidinylmethyl)-7-hydroxy-8-allyl-cumarin hydrochloride 25 g of 4-methyl-7-hydroxy-8-allylcoumarin are mixed with 300 ml of absolute ethanol, 8.3 g of pyrrolidine and 3.4 g of paraformaldehyde. The procedure then is the same as in example 1 until the precipitation of the hydrochloride. The precipitate is separated and then crystallized with ethanol; after filtering and drying the crystals, hydrochloride of the 4-methyl-6-(1-pyrrolidinylmethyl)-7-hydroxy-8-allylcoumarin is obtained.

MP 116°, Rf 0.62[thin layer chromatography (silica) chloroform-methanol-acetic acid-water (25+15+4+2)].

EXAMPLE 13

4-methyl-6-diethylaminomethyl-7-hydroxy-8-allyl-cumarin hydrochloride 25 g of 4-methyl-7-hydroxy-8-allylcoumarin are mixed with 350 ml of ethanol, 8.9 g of diethylamine and 3.9 g of paraformaldehyde. The mixture is refluxed for 60 hours, being kept in constant agitation meanwhile; the ethanol is then evaporated in vacuum. The residue is gathered with ethyl acetate and the organic solution is extracted with hydrochloric acid 1N. The aqueous acid layer is alkalinized with sodium bicarbonate and then extracted with methylene chloride. The methylene chloride solution is dried on anhydrous sodium sulfate, filtered and then the solvent is eliminated in vacuum. The residue is gathered with ethyl acetate and the formation of crystalline hydrochloride is achieved by adding gaseous hydrochloric acid. The precipitate is separated and then crystallized with isopropanol; after filtering and drying the crystals, hydrochloride of 4-methyl-6-diethylaminomethyl-7-hydroxy-8-allylcoumarin is obtained.

MP 188°, Rf 0.72[thin layer chromatography (silica) chloroform-methanol-acetic acid-water (25+15+4+2)].

EXAMPLE 14

4-methyl-6-(1-piperidinylmethyl)-7-hydroxy-8-allyl-cumarin hydrochloride 25 g of 4-methyl-7-hydroxy-8-allylcoumarin are mixed with 300 ml of ethanol, 9.9 g of piperidine and 3.4 g of paraformaldehyde. The mixture is refluxed for 96 hours, being kept constantly agitated meanwhile. The ethanol is evaporated in vacuum, after which the procedure is the same as for example 8 until precipitation of the hydrochloride. The precipitate is separated and then crystallized with ethanol, after filtering and drying the crystals, hydrochloride of 4-methyl-6-(1-piperidinylmethyl)-7-hydroxy-8-allylcoumarin is obtained.

MP 234°, Rf 0.84[thin layer chromatography (silica) chloroform-methanol-water-ammonium hydroxide 32% (130+25+2.8+0.5)].

EXAMPLE 15

4-methyl-6-[(4-hydroxy-1-piperidinyl)methyl]-7-hydroxy-8-allylcumarin hydrochloride 30 g of 4-methyl-7-hydroxy-8-allylcoumarin are mixed with 300 ml of ethanol, 14.1 g of 4-hydroxypiperidine and 4.2 g of paraformaldehyde. The procedure is then the same as for example 8 until precipitation of the hydrochloride. The precipitate is separated and then crystallized with ethanol; after filtering and drying the crystals, hydrochloride of the 4-methyl-6-[(4-hydroxy-1-piperidinyl)methyl]-7-hydroxy-8-allylcoumarina is obtained.

MF 252°, Rf 0.55[thin layer chromatography (silica) chloroform-methanol-acetic acid-water (25+15+4+2)].

EXAMPLE 16

4-methyl-6-[(3-hydroxy-1-piperidinyl)methyl]-7-hydroxy-8-allylcumarin hydrochloride 30 g of 4-methyl-7-hydroxy-8-allylcoumarin are mixed with 300 ml of ethanol, 14.1 g of 3-hydroxypiperidine and 4.2 g of paraformaldehyde. The mixture is refluxed for 24 hours, being kept in constant agitation meanwhile. The ethanol is evaporated in vacuum and the procedure is then the same as for example 13 until the formation of hydrochloride. The precipitate is separated and then crystallized from ethanol solution by adding ethyl acetate; after filtering and drying the crystals, hydrochloride of 4-methyl-6-[(3-hydroxy-1-piperidinyl)methyl]-7-hydroxy-8-allylcoumarin is obtained.

MP 184°, Rf 0.46[thin layer chromatography (silica) chloride of methylene-ethyl acetate-methanol (70+30+5)] is obtained.

EXAMPLE 17

3-(2-diethylaminoethyl)-4-methyl-6-(4-morpholinylmethyl)-7-hydroxy-8-chlorocumarin dihydrochloride 6.19 g of 3-(2-diethylaminoethyl)-4-methyl-7-hydroxy-8-chlorocoumarin are mixed with 200 ml of ethanol, 3.5 g of morpholine and 1.7 g of aqueous solution of 35% formaldehyde. The mixture is refluxed for 24 hours, being kept in constant agitation meanwhile. The ethanol is then evaporated in vacuum and the residue is gathered with ethyl acetate; a suspension is thus formed which is then filtered; the organic solution is extracted with hydrochloric acid 1N. The aqueous acid layer is alkalinized with sodium bicarbonate and then extracted with methylene chloride. The methylene chloride solution is dried on anhydrous sodium sulfate and, after filtration, the solvent is eliminated in vacuum. The residue is gathered with ethyl acetate and the formation of crystalline hydrochloride is achieved by adding gaseous hydrochloric acid. The precipitate is separated and crystallized from 95% ethanol; after filtering and drying the crystals, hydrochloride of 3-(2-diethylaminoethyl)-4-methyl-6-(4-morpholinylmethyl)-7-hydroxy-8-chlorocoumarin is obtained.

MP 174°, Rf 0.56[thin layer chromatography (silica) chloroform-methanol-water-ammonium hydroxide 32% (130+25+2.8+0.5)].

EXAMPLE 18

Ethyl ester of [3-(2-diethylaminoethyl)-4-methyl-6-(4-morpholinylmethyl)-8-chlorocumarin-7-yl]oxyacetic acid dihydrochloride 18 g of 3-(2-diethylaminoethyl)-4-methyl-6-(4-morpholinylmethyl)-7-hydroxy-8-chlorocoumarin are mixed with 300 ml of acetone, 12.2 g of potassium carbonate and 5.4 g of ethyl chloroacetate; the mixture is gradually brought to the boiling point, being kept in constant agitation meanwhile, and then refluxed for 24 hours. The solvent is then evaporated in vacuum. The residue is gathered with 300 ml of toluene and the mixture is treated with water. The toluenic layer is separated and then extracted with hydrochloric acid 1N; the aqueous acid solution is alkalinized with sodium bicarbonate; a suspension is thus formed which is then filtered. The precipitate is vacuum dried and then gathered with toluene; the formation of crystalline hydrochloride is achieved by addition of gaseous hydrochloric acid.

The precipitate is separated and crystallized from ethanol; after filtering and drying the crystals, hydrochloride of the ethyl ester of [3-(2-diethylaminoethyl)-4-methyl-6-(4-morpholinylmethyl)-8-chlorocoumarin-7-yl]oxy acetic acid is obtained.

MP 182°, Rf 0.62[thin layer chromatography (silica) chloroform-methanol-acetic acid-water (25+15+4+2)].

EXAMPLE 19

3-(2-diethylaminoethyl)-4-methyl-6-(4-morpholinylmethyl)-7-allyloxy-8-chlorocumarin hydrochloride 16 g of 3-(2-diethylaminoethyl)-4-methyl-6-(4-morpholinylmethyl)-7-hydroxy-8-chlorocoumarin are mixed with 300 ml of acetone, 10.8 g of potassium carbonate and 4.8 g of allylbromide. The procedure is then the same as for example 18 until the precipitation of the hydrochloride. The precipitate is separated and crystallized from ethanolic solution by adding ethyl ether; after filtering and drying the crystals, hydrochloride of 3-(2-diethylaminoethyl)-4-methyl-6-(4-morpholinylmethyl)-7-allyloxy-8-chlorocoumarin is obtained.

MP 150°, Rf 0.35[thin layer chromatography (silica) chloroform-methanol-acetic acid-water (25+15+4+2)] is obtained.

EXAMPLE 20

Ethyl ester of 2-[3-(2-diethylaminoethyl)-4-methyl-6-(4-morpholinylmethyl)-8-chlorocumarin-7-yl]oxy-2-methylpropionic acid dihydrochloride 16 g of 3-(2-diethylaminoethyl)-4-methyl-6-(4-morpholinylmethyl)-7-hydroxy-8-chlorocoumarin are mixed with 300 ml of toluene and 1 g of sodium hydride; the mixture is gradually heated to a temperature of 60°, being kept in constant agitation in the meantime; after thirty minutes' heating the solvent is evaporated in vacuum. The residue is solubilized with 100 ml of dimethylsulfoxide and 7.6 g of ethyl α-bromoisobutyrate are added to the solution, which is kept at room temperature; after 48 hours 300 ml of toluene are added and the organic mixture is washed with water. The toluenic solution is extracted with hydrochloric acid 1N and the acid aqueous solution, after being alkalinized with sodium carbonate, is extracted with methylene chloride. The methylene chloride solution is dried on anhydrous sodium sulfate, filtered and the solvent is then eliminated in vacuum. The residue is gathered with toluene and the formation of crystalline hydrochloride is achieved by adding gaseous hydrochloric acid. The precipitate is separated and crystallized from ethanol; after filtering and drying the crystals, dihydrochloride of the ethyl ester of 2-[3-(2-diethylaminoethyl)-4-methyl-6-(4-morpholinylmethyl)-8-chlorocoumarin-7-yl]oxy-2-methylpropionic acid is obtained.

MP 148°, Rf 0.51[thin layer chromatography (silica) chloroform-methanol-acetic acid-water (25+15°4+2)].

EXAMPLE 21

4-methyl-6-(4-morpholinylmethyl)-7-hydroxy-8-chlorocumarin hydrochloride 20 g of 4-methyl-7-hydroxy-8-chlorocoumarin are mixed with 300 ml of ethanol, 16.5 g of morpholine and 8 g of 35% formaldehyde aqueous solution. The mixture is refluxed for 48 hours, being kept in constant agitation meanwhile, and after 12 hours a suspension is obtained which is then filtered. The precipitate is dissolved in methylene chloride and the organic solution is extracted with aqueous solution of 10% acetic acid; the organic solution is then extracted (3 times) with hydrochloric acid 1N. The aqueous hydrochloric layer is alkalinized with sodium bicarbonate; a suspension is thus formed which is then filtered. The precipitate is vacuum dried and then treated with ethyl acetate; the precipitation of the crystalline hydrochloride is achieved by adding gaseous hydrochloric acid. The precipitate is then separated and crystallized from methanol. After filtering and drying the crystals, hydrochloride of 4-methyl-6-(4-morpholinylmethyl)-7-hydroxy-8-chlorocoumarin is obtained.

MP 227°, Rf 0.80 [thin layer chromatography (silica) chloroform-methanol-acetic acid-water (25+15+4+2)] is obtained.

EXAMPLE 22

4-methyl-6-diethylaminomethyl-7-hydroxy-8-chlorocumarin hydrochloride 21 g of 4-methyl-7-hydroxy-8-chlorocoumarin are mixed with 180 ml of ethanol, 20 ml of chloroform, 9.5 of of diethylamine and 11.2 g of 35% aqueous formaldehyde solution. The mixture is refluxed for 20 hours, being kept in constant agitation meanwhile; the ethanol and chloroform are evaporated in vacuum. The residue is solubilized in the methylenechloride-ethyl acetate-methanol mixture (7+3+1) and the solution is used for a chromatographic separation on silica, eluting with the same mixture of solvents. 4-methyl-6-diethylaminomethyl-7-hydroxy-8-chlorocoumarin is thus obtained. It is then treated with ethyl acetate and then, by adding gaseous hydrochloric acid, crystalline hydrochloride is formed. The precipitate is separated and crystallized from ethyl acetate. After filtering and drying the crystals, hydrochloride of 4-methyl-6-diethylaminomethyl-7-hydroxy-8-chlorocoumarin is obtained.

MP 202°, Rf 0.67 [thin layer chromatography (silica) chloroform-methanol-acetic acid-water (25+15+4+2)].

EXAMPLE 23

4-phenyl-6-(4-morpholinylmethyl)-7-hydroxy-8-chlorocumarin hydrochloride 20 g of 4-phenyl-7-hydroxy-8-chloro-coumarin are mixed with 300 ml of ethanol, 12.1 g of morpholine and 4.2 g of paraformaldehyde. The mixture is refluxed for 96 hours, being constantly agitated in the meantime; it is brought to room temperature and after 12 hours a suspension is obtained which is then filtered. The precipitate is dissolved in hydrochloric acid 1N and the resulting solution is extracted (3 times) with methylene chloride. Evaporation of the solvent produces a methylene chloride solution from which a chloride residue is obtained. The precipitate is crystallized from ethyl acetate; after filtering and drying the crystals, hydrochloride of 4-phenyl-6-(4-morpholinylmethyl)-7-hydroxy-8-chlorocoumarin is obtained.

MP 225°, Rf 0.79 [thin layer chromatography (silica) chloroform-methanol-water-ammonium hydroxide 32% (130+25+2.8+0.5)].

EXAMPLE 24

3-(2-diethylaminoethyl)-4-methyl-6-(4-morpholinylmethyl)-7-methoxy-8-chlorocumarin dihydrochloride 24.5 g of 3-(2-diethylaminoethyl)-4-methyl-6-(4-morpholinylmethyl)-7-hydroxy-8-chlorocoumarin are mixed with 300 ml of toluene and 1.6 g of sodium hydrate; the mixture is gradually heated to 60°, being constantly agitated meanwhile; after 30 minutes' heating the solvent is evaporated in vacuum. The residue is solubilized with 100 ml of dimethylsulfoxide and 7.5 g of dimethyl sulfate are added to the solution, which is kept at a temperature of 80°; after 48 hours 300 ml of toluene are added and the organic mixture is washed with water. The toluene solution is extracted with hydrochloric acid 1N and the acid aqueous solution is alkalinized with sodium bicarbonate; a suspension is thus formed which is then filtered. The precipitate is vacuum dried and gathered with toluene; crystalline hydrochloride is formed by the addition of gaseous hydrochloric acid.

The precipitate is separated and crystallized from ethanol. After filtering and drying the crystals, dihydrochloride of 3-(2-diethylaminoethyl)-4-methyl-6-(4-morpholinylmethyl)-7-methoxy-8-chlorocoumarin is obtained.

MP 181°, Rf 0.41 [thin layer chromatography (silica) chloroform-methanol-acetic acid-water (25+15+4+2)].

EXAMPLE 25

4-methyl-6-dimethylaminomethyl-7-hydroxy-8-chlorocumarin hydrochloride 30 g of 4-methyl-7-hydroxy-8-chlorocoumarin are mixed with 200 ml of ethanol, 38.2 g of 33% dimethylamine aqueous solution and 8.5 g of paraformaldehyde. The mixture is refluxed for 72 hours, being constantly agitated in the meantime. The ethanol is evaporated in vacuum. The procedure is then the same as for example 8 until the precipitation of the hydrochloride. The precipitate is separated and crystallized from ethyl acetate; after filtering and drying the crystals, hydrochloride of 4-methyl-7-hydroxy-6-dimethylaminomethyl-7-hydroxy-8-chlorocoumarin is obtained.

MP 238°, Rf 0.27 [thin layer chromatography (silica) chloroform-methanol-acetic acid-water (25+15+4+2)].

EXAMPLE 26

4,8-dimethyl-6-dimethylaminomethyl-7-hydroxycumarin hydrochloride 30 g of 4,8-dimethyl-7-hydroxycoumarin are mixed with 300 ml of ethanol, 50 ml of chloroform, 27.1 g of 33% dimethylamine aqueous solution and 6 g of paraformaldehyde. The mixture is refluxed for 48 hours, being constantly agitated meanwhile. The ethanol and chloroform are evaporated in vacuum. The procedure is then the same as for example 13 until the formation of hydrochloride. The precipitate is separated and then crystallized from 95% ethanol; after filtering and drying the crystals, hydrochloride of 4,8-dimethyl-6-dimethylaminomethyl-7-hydroxycoumarin is obtained.

MP 252°, Rf 0.77 [thin layer chromatography (silica) chloroform-methanol-acetic acid-water (25+15+4+2)].

EXAMPLE 27

4,8-dimethyl-6-(4-morpholinylmethyl)-7-hydroxycoumarin hydrochloride 30 g of 4,8-dimethyl-7-hydroxycoumarin are mixed with 300 ml of 85% aqueous ethanol, 13.8 g of morpholine and 4.8 g of paraformaldehyde. The mixture is refluxed for 96 hours, being constantly agitated meanwhile; it is then brought to a temperature of 5° and after 12 hours a suspension is obtained which is then filtered. The precipitate is vacuum dried and then treated with ethyl acetate. Precipitation of the crystalline hydrochloride is achieved by adding gaseous hydrochloric acid. The precipitate is separated and crystallized from ethanol. After filtering and drying the crystals, hydrochloride of 4,8-dimethyl-6-(4-morpholinylmethyl)-7-hydroxy coumarin is obtained.

MP 238°, Rf 0.84 [thin layer chromatography (silica) chloroform-methanol-acetic acid-water (130+25+2.8+0.5)].

EXAMPLE 28

4-phenyl-6-dimethylaminomethyl-7-hydroxy-8-allylcumarin hydrochloride 18 g of 4-phenyl-7-hydroxy-8-allyl coumarin are mixed with 250 ml of ethanol, 23.4 g of 18.5% dimethylamine aqueous solution and 5.6 g of 35% formaldehyde aqueous solution. The mixture is refluxed for 60 hours, being constantly agitated meanwhile. The ethanol is evaporated in vacuum. The procedure is then the same as for example 8 until the precipitation of the hydrochloride. The precipitate is separated and cyrstallized from 95% ethanol. After filtering and drying the crystals, hydrochloride of 4-phenyl-6-dimethylaminomethyl-7-hydroxy-8-allylcoumarin is obtained.

MP 199°, Rf 0.82 [thin layer chromatography (silica) chloroform-methanol-acetic acid-water (25+15+4+2)].

EXAMPLE 29

Examples of injectable pharmaceutical compositions (the active compounds can be identified from Table 1 of the general description)

Preparation No. 1

Preparation with antitumoral and antimetastatic activity in the form of an aqueous solution Composition:
a. one freeze-dried flacon contains:

| | |
|---|---|
| compound 19 (Ex. 1) | mg 10 |
| mannitol | mg 10 | b. one vial of solvent contains:

| | |
|---|---|
| sodium chloride | mg 18 |
| apyrogenetic distilled water | ml 2 |

Preparation No. 2

Preparation with platelet antiaggregating activity in the form of an aqueous solution Composition:
a. one freeze-dried flacon contains:

| | |
|---|---|
| compound 121 (Ex. 13) | mg 30 |
| mannitol | mg 30 | b. one 5 ml vial of solvent contains:

| | |
|---|---|
| sodium chloride | mg 45 |
| apyrogenetic distilled water | ml 5 |

Preparation No. 3

Preparation with an antitumoral and antimetastatic activity in the form of an aqueous solution Composition:
a. one freeze-dried vial contains:

| | |
|---|---|
| compound 26 (Ex. 3) | mg 50 |
| mannitol | mg 30 | b. one 3 ml vial of solvent contains:

| | |
|---|---|
| sodium chloride | mg 27 |
| apyrogenetic distilled water | ml 3 |

Preparation No. 4

Preparation with platelet antiaggregating activity in the form of an aqueous solution Composition:
a. one freeze-dried vial contains:

| | |
|---|---|
| compound 117 (Ex. 12) | mg 40 |
| mannitol | mg 25 | b. one 5 ml vial of solvent contains:

| | |
|---|---|
| sodium chloride | mg 45 |
| apyrogenetic distilled water | ml 5 |

EXAMPLE 30

Examples of pharmaceutical compositions by oral route (The compounds can be identified from Table 1 of the general description)

Preparation No. 1

Preparation with an antitumoral and platelet antiaggregating activity in tablet form Composition:
each tablet contains:

| | |
|---|---|
| compound 19 (Ex. 1) | mg. 20 |
| microcrystalline cellulose | mg. 150 |
| lactose | mg. 20 |
| starch | mg. 10 |
| magnesium stearate | mg. 5 |

Preparation No. 2

Preparation with a platelet antiaggregating activity in the form of sugar-coated pills Composition:
each pill contains:

| | |
|---|---|
| compound 124 (Ex. 14) | mg. 30 |
| carboxymethyl cellulose | mg. 150 |
| starch | mg. 15 |
| shellac | mg. 10 |
| saccharose | mg. 35 |
| colouring | mg. 0.5 |

Preparation No. 3

Preparation with an antitumoral and antimetastatic-activity in the form of gelatinous opercula Composition:
each gelatinous operculum contains:

| | |
|---|---|
| compound 26 (Ex. 3) | mg. 40 |
| lactose | mg. 100 |
| gastroresistant varnish | mg. 5 |

Preparation No. 4

Preparation with a platelet antiaggregating activity in capsule form

Composition:
each soft gelatine capsule contains:

| | |
|---|---|
| compound 28 (Ex. 5) | mg. 50 |
| vegetable oil | mg. 200 |
| beeswax | mg. 20 |
| gelatine | mg. 150 |
| glycerine | mg. 50 |
| coloring | mg. 3 |

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method for the treatment of Lewis lung carcinoma which comprises administering an effective antitumor or antimetastatic amount of 4-methyl-6-dimethylaminomethyl-7-hydroxy-8-allylcoumarin, or a pharmaceutically acceptable salt thereof.

* * * * *